United States Patent
Hood et al.

(10) Patent No.: US 9,884,804 B2
(45) Date of Patent: Feb. 6, 2018

(54) SURFACE TREATED CARBON CATALYSTS PRODUCED FROM WASTE TIRES FOR FATTY ACIDS TO BIOFUEL CONVERSION

(71) Applicant: UT-Battelle, LLC, Oak Ridge, TN (US)

(72) Inventors: Zachary D. Hood, Atlanta, GA (US); Shiba P. Adhikari, Winston Salem, NC (US); Marcus W. Wright, King, NC (US); Abdessadek Lachgar, Winston Salem, NC (US); Yunchao Li, Knoxville, TN (US); Amit K. Naskar, Knoxville, TN (US); Mariappan Parans Paranthaman, Knoxville, TN (US)

(73) Assignees: UT-BATTELLE, LLC, Oak Ridge, TN (US); UNIVERSITY OF TENNESSEE RESEARCH FOUNDATION, Knoxville, TN (US)

( * ) Notice: Subject to any disclaimer, the term of this patent is extended or adjusted under 35 U.S.C. 154(b) by 0 days.

(21) Appl. No.: 15/163,434

(22) Filed: May 24, 2016

(65) Prior Publication Data
US 2017/0342014 A1 Nov. 30, 2017

(51) Int. Cl.
- *C07C 67/08* (2006.01)
- *C01B 31/08* (2006.01)
- *B01J 31/02* (2006.01)
- *B01J 35/02* (2006.01)

(Continued)

(52) U.S. Cl.
CPC ........... *C07C 67/08* (2013.01); *B01J 31/0225* (2013.01); *B01J 35/026* (2013.01);
(Continued)

(58) Field of Classification Search
CPC .... C07C 67/08; C01B 31/081; B01J 31/0225; B01J 35/026; B01J 35/1057;
(Continued)

(56) References Cited

U.S. PATENT DOCUMENTS 3,823,221 A * 7/1974 Wakefield et al. ...... C08K 3/04
106/405
3,886,088 A * 5/1975 DeJong ................. C01B 31/081
201/2.5

(Continued)

FOREIGN PATENT DOCUMENTS

CN 101003695 A 7/2007
CN 102214516 A 10/2011
(Continued)

OTHER PUBLICATIONS

"Biochar based solid acid catalyst for biodiesel production," Amir Mehdi Dehkhoda et al. Applied Catalysis A: General 382(2010), pp. 197-204.*

(Continued)

*Primary Examiner* — Patricia L. Hailey
(74) *Attorney, Agent, or Firm* — Fox Rothschild LLP

(57) ABSTRACT

A method of making solid acid catalysts includes the step of sulfonating waste tire pieces in a first sulfonation step. The sulfonated waste tire pieces are pyrolyzed to produce carbon composite pieces having a pore size less than 10 nm. The carbon composite pieces are then ground to produce carbon composite powders having a size less than 50 μm. The carbon composite particles are sulfonated in a second sulfonation step to produce sulfonated solid acid catalysts. A method of making biofuels and solid acid catalysts are also disclosed.

22 Claims, 15 Drawing Sheets

(51) Int. Cl.
*B01J 35/10* (2006.01)
*B01J 37/08* (2006.01)
*B01J 37/00* (2006.01)

(52) U.S. Cl.
CPC ....... *B01J 35/1057* (2013.01); *B01J 35/1061* (2013.01); *B01J 37/0072* (2013.01); *B01J 37/084* (2013.01); *C01B 31/081* (2013.01); *B01J 2231/49* (2013.01); *B01J 2531/004* (2013.01)

(58) Field of Classification Search
CPC .. B01J 35/1061; B01J 37/0072; B01J 37/084; B01J 2231/49
USPC ........ 502/174, 216; 423/449.7; 44/435, 628; 106/274
See application file for complete search history.

(56) References Cited

U.S. PATENT DOCUMENTS

| | | | |
|---|---|---|---|
| 4,002,587 A * | 1/1977 | Watanabe | C01B 31/089 264/105 |
| 5,728,361 A * | 3/1998 | Holley | C09C 1/48 423/449.6 |
| 5,744,668 A | 4/1998 | Zhou et al. | |
| 5,961,946 A * | 10/1999 | Takegawa | C09C 1/482 423/449.7 |
| 5,965,479 A * | 10/1999 | Suzuki | B01J 20/06 423/447.5 |
| 6,297,293 B1 | 10/2001 | Bell et al. | |
| 6,547,710 B1 | 4/2003 | Patel et al. | |
| 6,737,445 B2 | 5/2004 | Bell et al. | |
| 6,802,897 B1 * | 10/2004 | Lackey | C08K 3/06 106/274 |
| 6,919,063 B2 | 7/2005 | Jang et al. | |
| 7,416,641 B2 | 8/2008 | Denison | |
| 7,497,929 B2 | 3/2009 | Karpetsky et al. | |
| 7,947,248 B2 * | 5/2011 | Hamby | C09C 1/48 366/342 |
| 7,993,780 B2 | 8/2011 | Jang et al. | |
| 8,013,130 B2 * | 9/2011 | Yanagawa | B01J 27/02 423/447.9 |
| 8,575,281 B2 * | 11/2013 | Yanagawa | B01J 27/02 525/505 |
| 9,441,113 B2 | 9/2016 | Naskar et al. | |
| 2002/0065333 A1 | 5/2002 | Bell et al. | |
| 2002/0114126 A1 | 8/2002 | Hirahara et al. | |
| 2008/0227996 A1 * | 9/2008 | Hara | B01J 31/0225 558/44 |
| 2009/0136849 A1 | 5/2009 | Yue et al. | |
| 2012/0263641 A1 * | 10/2012 | Chung | B29B 17/02 423/449.3 |
| 2014/0371385 A1 * | 12/2014 | Verberne | C09C 1/482 524/571 |
| 2015/0017528 A1 | 1/2015 | Roberts et al. | |
| 2015/0021525 A1 * | 1/2015 | Naskar | C09C 1/482 252/502 |
| 2016/0254543 A1 * | 9/2016 | Naskar | C09C 1/482 429/231.8 |
| 2016/0351346 A1 * | 12/2016 | Naskar | H01G 11/34 |

FOREIGN PATENT DOCUMENTS

| | | |
|---|---|---|
| FR | 2357616 A1 | 2/1978 |
| KR | 101147788 B1 | 5/2012 |
| WO | 200129150 | 4/2001 |
| WO | 2011010323 A1 | 1/2011 |

OTHER PUBLICATIONS

"New sulfonic acid ion-exchange resins for the preesterification of different oils and fats with high content of free fatty acids,"

Bernhard M. E. Russbueldt, et al. Applied Catalysis A: General 362 (2009), pp. 47-57.*
Y. Zhou et al.: "Polyaniline/multi-walled carbon nanotube composites with core-shell structures as supercapacitor electrode materials", Electrochim. Acta, 2010, 55, 3904-3908.
X. Xia et. al.: "Reduced-graphene oxide-molybdenum oxide/polyaniline ternary composite for high energy density supercapacitors: Synthesis and properties" J. Mater. Chem., 2012, 22, 8314.
K. B. Hatzell et al.:"Composite Manganese Oxide Percolating Networks As a Suspension Electrode for an Asymmetric Flow Capacitor", ACS Appl. Mater. Interfaces, 2014, 6, 8886-8893.
Q. Wu et al.: "Supercapacitors Based on Flexible Graphene/Polyaniline Nanofiber Composite Films" ACS Nano, 2010, 4, 1963-1970.
Z. Lei et al.: "Growth of Polyaniline on Hollow Carbon Spheres for Enhancing Electrocapacitance", J. Phys. Chem. C, 2010, 114, 19867-19874.
X. Wang et al.: Crosslinked polyaniline nanorods with improved electrochemical performance as electrode material for supercapacitors, J. Mater. Chem. A, 2014, 2, 12323.
C. Xia et al.: "Highly Stable Supercapacitors with Conducting Polymer Core-Shell electrodes for Energy Storage Applications", Adv. Energy Mater., 2015.
L. Wang et al.: "Hierarchical Nanocomposites of Polyaniline Nanowire Arrays on Reduced Graphene Oxide Sheets for Supercapacitors" Sci. Rep., 2013, 3, 3568.
A. Du Pasquier et al.: "Li4Ti5O12/poly(methyl)thiophene asymmetric hybrid electrochemical device" J. Power Sources, 2004, 125, 95-102.
J. S. Lee et al.: "A metal-oxide nano?ber-decorated three dimensional graphene hybrid nanostructured flexible electrode for high-capacity electrochemical capacitors", J. Mater. Chem. A, 2014, 2, 11922.
R. B. Rakhi et al.: "Conducting polymer/carbon nanocoil composite electrodes for efficient supercapacitors", J. Mater. Chem., 2012, 22, 5177.
Shu et al: "Synthesis of biodiesel from waste vegetable oil with large amounts of free fatty acids using a carbon-based solid acid catalyst", J. Applied Energy 2010, 87, 2589.
Canakci et al.: "Biodiesel Production From Oils and Fats With High Free Fatty Acids", Transactions-American Society of Agricultural Engineers 2001, 44, 1429.
Ma et al.: "Biodiesel production: a review", Bioresource technology 1999, 70, 1.
Peng et al.: "Biodiesel production from waste oil feedstocks by solid acid catalysis", Process Safety and Environmental Protection 2008, 86, 441.
Boota et al.: "Waste Tire Derived Carbon-Polymer Composite Paper as Pseudocapacitive Electrode with Long Cycle Life", ChemSusChem 2015, 8, 3576.
Naskar et al.: "Tailored recovery of carbons from waste tires for enhanced performance as anodes in lithium-ion batteries", RSC Advances 2014, 4, 38213.
Zhi et al.: "Effects of Pore Structure on Performance of an Activated-Carbon Supercapacitor Electrode Recycled from Scrap Waste Tires", ACS Sustainable Chemistry & Engineering 2014, 2, 1592.
Chen et al.: "Gold Nanocages: Bioconjugation and Their Potential Use as Optical Imaging Contrast Agents", Nano letters 2005, 5, 473.
Deshmane et al.: "A comparative study of solid carbon acid catalysts for the esterification of free fatty acids for biodiesel production. Evidence for the leaching of colloidal carbon", Bioresource technology 2013, 147, 597.
Toda et al.: "Green chemistry: Biodiesel made with sugar catalyst", Nature 2005, 438, 178.
Shu et al.:"Synthesis of biodiesel from cottonseed oil and methanol using a carbon-based solid acid catalyst", Fuel Processing Technology 2009, 90, 1002.
Jacobson et al.: "Solid acid catalyzed biodiesel production from waste cooking oil" Applied Catalysis B: Environmental 2008, 85, 86.

(56) References Cited

OTHER PUBLICATIONS

Sani, Y. et al.:"Activity of solid acid catalysts for biodiesel production: A critical review", Applied Catalysis A: General 2014, 470, 140.
Naskar et al.: "Tailored recovery of carbons from waste tires for enhanced performance as anodes in lithium-ion batteries." RSC Adv., 2014, 4, 38213.
Zhi et al.: "Effects of Pore Structure on Performance of An Activated-Carbon Supercapacitor Electrode Recycled from Scrap Waste Tires", ACS Sustainable Chem. Eng. 2014, 2, 1592?1598.
Hummers et al., "Preparation of graphitic oxide", J Am Chem Soc (1958) 80(6): 1339.
Lin et al. "Surface functional characteristics (C, 0, S) of waste tire-derived carbon black before and after steam activation", J Atr & Waste Manage. Assoc. (2008) 58: 78-84.
Tang et al., "Thermal plasma pyrolysis of used tires for carbon black recovery", Journal of Materials Science (2005) 40(14): 3817-3819.
Wojtowicz et al., "Carbon black derived from waste tire pyrolysis", Advanced Fuel Research, Inc. (n.d.). (7 pages).
J. Voelcker, Green Car Reports, 2014.
San Miguel et al. "Pyrolysis of Tire Rubber: Porosity and Adsorption Characteristics of the Pyrolytic Chars",, Ind. Eng. Chem. Res., 2006, 37, 2430-2435.
A. Quek et al: "Liquefaction of waste tires by pyrolysis for oil and chemicals—A review", J. Anal. Appl. Pyrolysis, 2013, 101, 1-16.
F. Béguin et al.: "Carbons and Electrolytes for Advanced Supercapacitors", Adv. Mater., 2014, 26, 2219-2251.
P. Simon et al.: "Charge storage mechanism in nanoporous", Trans. A. Math. Phys. Eng. Sci., 2010, 368, 3457-3467.
M.-M. Titirici, et al.: "Sustainable carbon materials", Chem. Soc. Rev., 2015, 44, 250-290.
E. M. Lotfabad et al.: "High-Density Sodium and Lithium Ion Battery Anodes from Banana Peels", ACS Nano, 2014, 8, 7115-7129.
H. Wang et al.: "Interconnected Carbon Nanosheets Derived from Hemp for Ultrafast Supercapacitors with High Energy", ACS Nano, 2013, 7, 5131-41.
J. Jiang et al.: "Evolution of disposable bamboo chopsticks into uniform carbon ?bers: a smart strategy to fabricate sustainable anodes for Li-ion batteries", Energy Environ. Sci., 2014, 7, 2670-2679.
L.-F. Chen et al.: "Flexible all-solid-state high-power supercapacitor fabricated with nitrogen-doped carbon nano?ber electrode material derived from bacterial cellulose", Energy Environ. Sci., 2013, 6, 3331.
M. Biswal et al.: "From dead leaves to high energy density supercapacitors", Energy Environ. Sci., 2013, 6, 1249.
P. Chen et al.: "Nitrogen-doped nanoporous carbon nanosheets derived from plant biomass: an efficient catalyst for oxygen reduction reaction", Energy Environ. Sci., 2014, 7, 4095-4103.
W. Qian et al.: "Human hair-derived carbon flakes for electrochemical supercapacitors", Energy Environ. Sci., 2013, 379-386.

J. Ding et al.: "Peanut shell hybrid sodium ion capacitor with extreme energy-power rivals lithium ion capacitors", Energy Environ. Sci., 2015, 8, 941-955.
J. Zhang et al.: "On the Configuration of Supercapacitors for Maximizing Electrochemical Performance", ChemSusChem, 2012, 5, 818-41.
T. Liu et al.: "Polyaniline and Polypyrrole Pseudocapacitor Electrodes with Excellent Cycling Stability", Nano Lett, 2014, 14, 2522-2527.
G. Wang et al."A review of electrode materials for electrochemical supercapacitors", Chem. Soc. Rev., 2012, 41, 797.
A. K. Naskar et al.: "Tailored recovery of carbons from waste tires for enhanced performance as anodes in lithium-ion batteries", RSC Adv., 2014, 4, 38213.
L. Wei et al.: "Hydrothermal Carbonization of Abundant Renewable Natural Organic Chemicals for High-Performance Supercapacitor Electrodes", Adv. Energy Mater., 2011, 1, 356-361.
J. Huang et al.: "Nanofiber Formation in the Chemical Polymerization of Aniline: A Mechanistic Study". Chemie—Int. Ed., 2004, 43, 5817-5821.
M. Boota et al.: "Towards High-Energy-Density Pseudocapacitive Flowable Electrodes by the Incorporation of Hydroquinone" ChemSusChem, 2015, 8, 835-843.
K. B. Hatzell et al.: "Effect of Oxidation of Carbon Material on Suspension Electrodes for Flow Electrode Capacitive Deionization", Environ. Sci. Technol., 2015, 150211062348002.
M. Boota, et al.: "Graphene-containing flowable electrodes for capacitive energy storage" Carbon N. Y., 2015, 92, 142-149.
C. Zhang et al.: Highlyporouscarbonspheresforelectrochemicalcapacitorsandcapacitiveflowablesuspensionelectrodes, Carbon N. Y., 2014, 77, 155-164.
M. Tagowska et al.: "Polyaniline nanotubules-anion effect on conformation and oxidation state of polyaniline studied by Raman Spectroscopy", Synth. Met., 2004, 142, 223-229.
S. Sharma et al.: "Chloroform vapour sensor based on copper/polyaniline nanocomposite", Sensors Actuators, B Chem., 2002, 85, 131-136.
M. A. Islam et al.: "Mesoporous and adsorptive properties of palm date seed activated carbon prepared via sequential hydrothermal carbonization and sodium hydroxide activation", Chem. Eng. J., 2015, 270, 187-195.
M. Boota et al.: "Activated Carbon Spheres as a Flowable Electrode in Electrochemical Flow Capacitors", Electrochem. Soc., 2014, 161, A1078-A1083.
K. B. Hatzell et al.: "Flowable Conducting Particle Networks in Redox-Active Electrolytes for Grid Energy Storage", J. Electrochem. Soc., 2015, 162, A5007-A5012.
J. Xu et al.: "Hierarchical Nanocomposites of Polyaniline Nanowire Arrays on Graphene Oxide Sheets with Synergistic Effect for Energy Storage", ACS Nano, 2010, 4, 5019-5026.
H.-P. Cong et al.: "Flexible graphene-polyaniline composite paper for high-performance supercapacitor", Energy Environ. Sci., 2013, 6, 1185.

* cited by examiner

Figure 1A
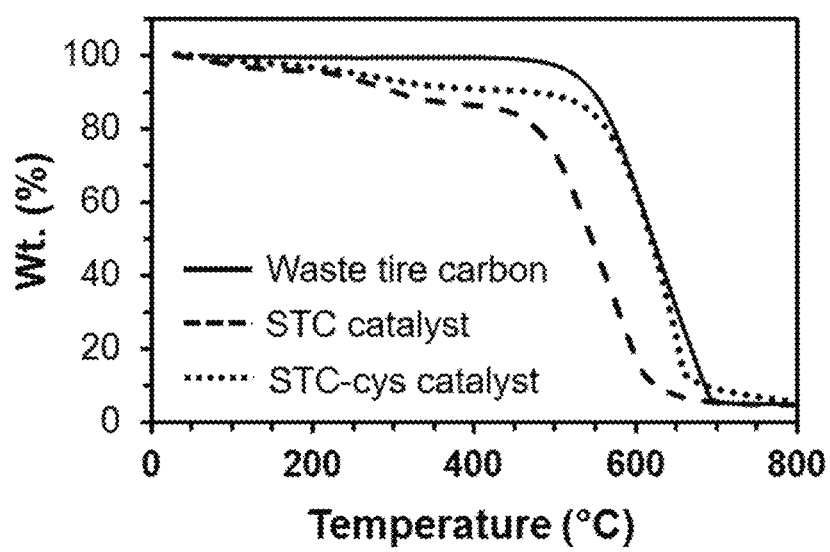
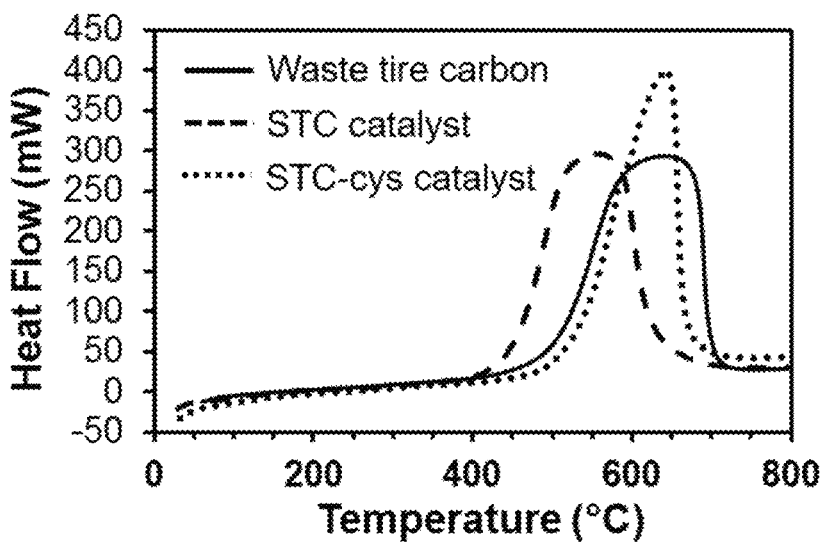
Figure 1B

Figure 3A  Figure 3B  Figure 3C
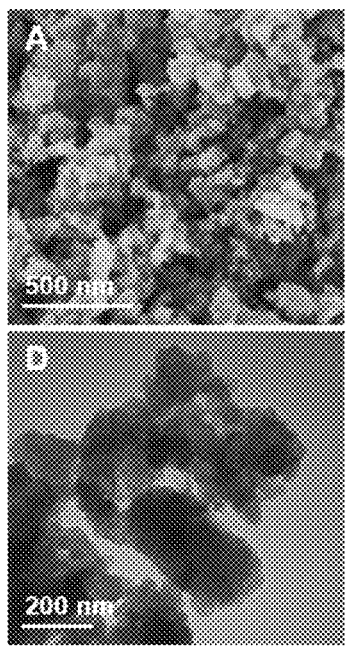 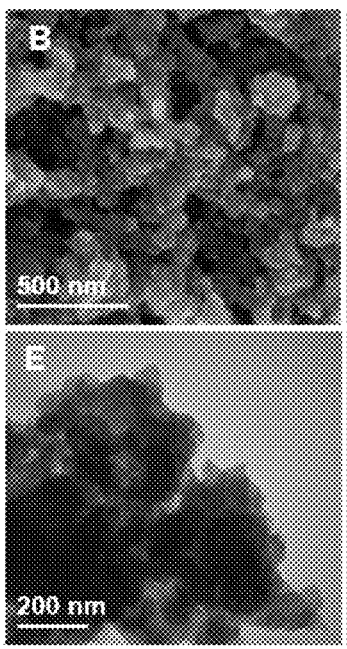 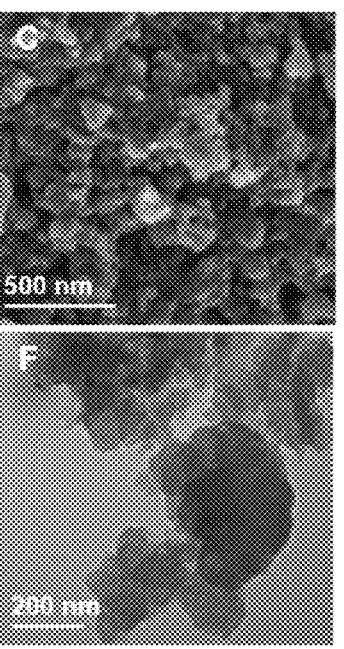
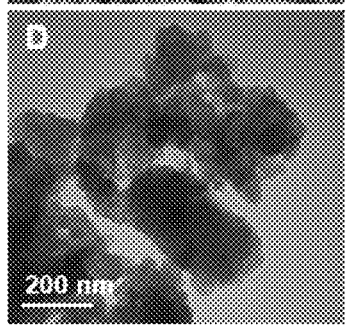 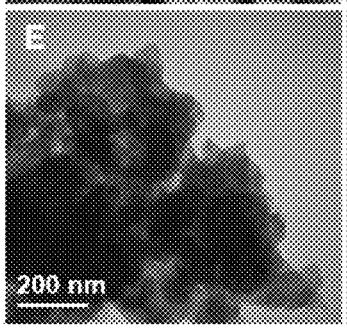 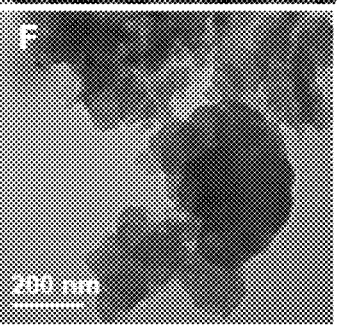
Figure 3D  Figure 3E  Figure 3F Figure 9A
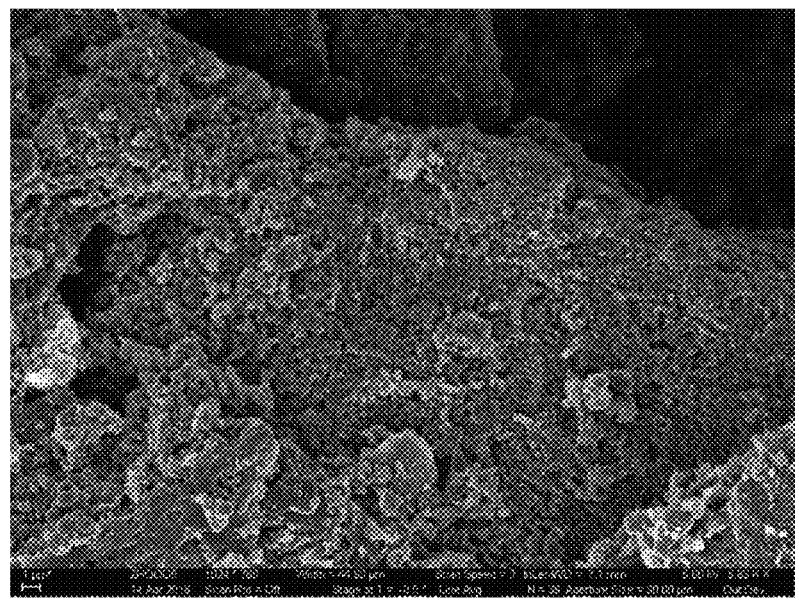
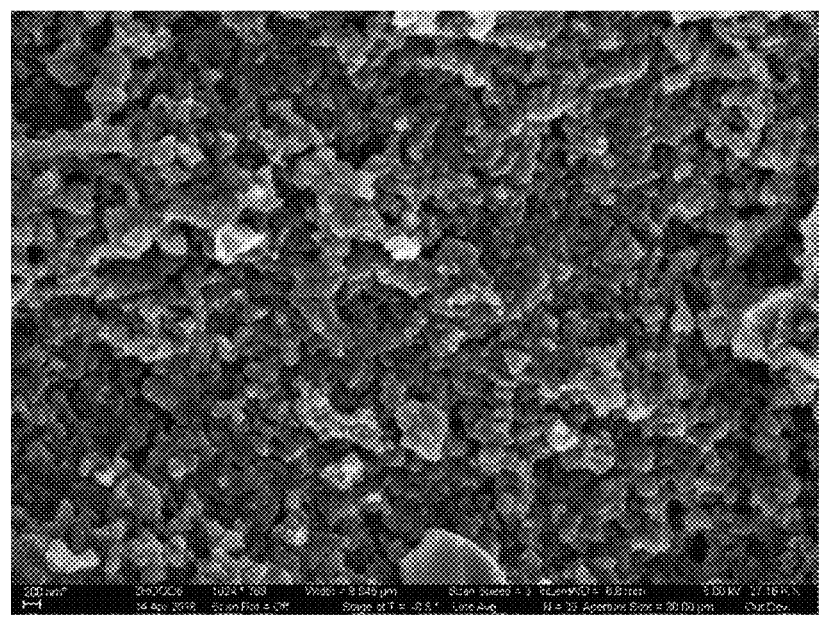
Figure 9 B

SURFACE TREATED CARBON CATALYSTS PRODUCED FROM WASTE TIRES FOR FATTY ACIDS TO BIOFUEL CONVERSION

STATEMENT REGARDING FEDERALLY SPONSORED RESEARCH

This invention was made with government support under contract No. DE-AC05-00OR22725 awarded by the U.S. Department of Energy. The government has certain rights in this invention.

FIELD OF THE INVENTION

This invention relates generally to biofuel production, and more particularly to methods and catalysts for biofuel production.

BACKGROUND OF THE INVENTION

The paradigm shift from consuming non-renewable fossil fuels to utilizing renewable biofuels necessitates economic supply chains and cheaper manufacturing routes in order for biofuels to have a competitive edge in the market. Biodiesel, a renewable fuel source, is both biodegradable and has a lower emission profile when compared to fossil fuels, rendering biodiesel as environmentally beneficial. Biodiesel is becoming more popular in both developed and underdeveloped countries since this fuel source can be synthesized from feedstocks such as animal fats, waste cooking oil, vegetable oils, amongst others renewable sources. Still, the production cost of biodiesel greatly relies on the selection of oil feedstock. Many cheap feedstocks for biodiesel production contain increased concentrations of free fatty acids (FFAs) such as waste fats and non-edible oils. Some of the most common FFAs include oleic, linoleic, linolinic, and palmitic acids. FFAs undergo saponification in the presence of a strong base used in the transesterification of triglycerides for the production of biodiesel, which compromises the overall biodiesel yield from different feedstocks and causes complications with the separation of biodiesel from alcohol. To prevent this problem, FFAs can be converted to usable biodiesel according to Equation (1) where a catalyst mediates the esterification reaction between the FFA and methanol:

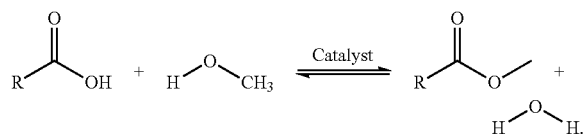

Equation 1

Since inexpensive feedstocks, such as waste cooking oil, contain high concentrations of FFAs, there exists a need for inexpensive catalysts that can better convert FFAs to usable biodiesel.

Homogeneous catalysts, such as $H_2SO_4$, have been widely demonstrated to catalyze both esterification and transesterification reactions for the production of biodiesel. However, $H_2SO_4$ suffers from several drawbacks, namely the fact that $H_2SO_4$ causes equipment corrosion and the resulting biodiesel necessitates neutralization. To avert this problem, different heterogeneous solid acid catalysts have been explored since such catalysts can be easily removed by filtration and reused for subsequent reactions. The utilization of heterogeneous catalysts also allows for greater yields of biodiesel while averting the unwanted saponification reaction from FFAs. Different materials have been demonstrated as heterogeneous solid acid catalysts, including Nafion, zeolites, La/zeolite beta, Amberlyst-15, among others. Although such catalysts show good activity to catalyze the esterification of FFAs, these materials come at an increased cost, which comprises the overall biodiesel production price. For this reason, the exploration of cheaper heterogeneous catalyst systems is necessitated to allow biodiesel to have a competitive edge in the market.

Recently, there has been increased interest in pyrolyzed waste tires since they serve as a cheap carbon source that can be used in various applications including Li-ion battery anodes, supercapacitors, and catalysts. Approximately 290 million tires are disposed annually in the United States, and it is estimated that 27 million scrap tires end up in landfills or monofills annually. Since tire rubber is non-biodegradable, this material poses inherent environmental concerns and serves as one of the most problematic sources of waste. The pyrolysis of different waste carbon materials to produce carbon black has been demonstrated. For example, the pyrolysis of wood, sucrose, and coconut shells produces carbon black, which costs $0.80/kg, $0.25/kg, and $0.25/kg respectively. In comparison, the pyrolysis of waste tire carbon costs about $0.06/kg, rendering this material as an attractive candidate to produce activated carbon. In turn, waste tires can be used for multiple applications rather than their disposal into landfills.

Carbon-based solid acid catalysts have been widely explored where their use in catalysis is mainly focused on the esterification of FFAs. These catalysts have been prepared from different sulfonated carbon sources, such as sugars, polymers, and high surface area silica-templated carbons. These materials contain sulfonic acid groups (—$SO_3H$), which catalyze the esterification of FFAs. The soft carbons show good initial performance in converting FFAs to monoesters, however, with increased use these carbons tend to leach acid sites, compromising their use to mass produce biodiesel. Therefore, more robust carbon supports are desired for biodiesel production. In addition to converting FFAs to monoesters (biofuel), the triglycerides present in used oil can be converted to esters (biofuel) and glycerin using the standard base catalysts.

SUMMARY OF THE INVENTION

A method of making solid acid catalysts includes the step of sulfonating waste tire pieces in a first sulfonation step. The sulfonated waste tire pieces are pyrolyzed to produce carbon composite pieces. The carbon composite powders derived from waste tire pieces are then ground to produce carbon particles having a size less than 50 µm and having a pore size less than 10 nm. The carbon particles can have a size of from 2 µm to 20 µm. The carbon particles can have a pore size of from 3 nm to 8 nm. The carbon particles are sulfonated in a second sulfonation step to produce sulfonated solid acid catalysts.

At least one of the sulfonation steps can be performed by soaking in a sulfuric acid bath. The sulfuric acid bath can be at least 5 M concentration. The sulfonation bath can have a temperature of between −20° C. to 200° C. The soaking can be for at least 10-20 minutes.

The method can further comprise the step of washing the sulfonated waste tire pieces. The washed sulfonated waste tire pieces can be pressed and heated into a sheet prior to the pyrolyzing step.

The pyrolyzing step can include heating the sulfonated waste tire pieces to from 900° C. to 1500° C. The second sulfonation step can comprise contacting the carbon particles with L-cysteine with water and heat, followed by a reduction step and an oxidation step.

A method of making biofuels includes the step of preparing a solid acid catalyst. The solid acid catalyst can be prepared by the steps of a) sulfonating waste tire pieces in a first sulfonation step; b) pyrolyzing the waste tire pieces to produce carbon composite pieces having a pore size less than 10 nm; c) grinding the pyrolyzed waste tire pieces to a particle size less than 50 μm; and, d) sulfonating the pyrolyzed sulfonated carbon in a second sulfonation step to produce sulfonated solid acid catalysts. A feedstock comprising free fatty acids is provided. The free fatty acids are esterified in the presence of the sulfonated solid acid catalysts.

The pyrolyzing step can include heating the sulfonated waste tire pieces to from 900° C. to 1500° C. The esterification can be performed in the presence of methanol. The free fatty acids can be either saturated or unsaturated. The free fatty acids can be at least one selected from the group consisting of formic acid, acetic acid, oleic acid, linoleic acid, linolinic acid, and palmitic acid, stearic acid, lauric acid, octadecadienoic acid, hexadecanoic acid, myristic acid, stearidonic acid, elaidic acid, gondoic acid, erucic acid, nervonic acid, mead acid, gadoleic acid, eicosenoic acid, erucic acid, pinolenic acid, stearidonic acid, arachidonic acid, eicosapentaenoic acid, and benzoic acid. The feedstock can include at least one selected from the group consisting of animal fats, waste cooking oil, and vegetable oil.

The second sulfonation step can include contacting the carbon particles with L-cysteine to produce sulfur containing carbon particles, contacting the sulfur containing particles with a reducing agent to produce reduced sulfur containing particles, and oxidizing the reduced sulfur containing particles to produce sulfonated solid acid catalysts. The L-cysteine can be contacted with the carbon particles using a hydrothermal method followed by a reduction step and an oxidation step to produce sulfonated solid acid catalysts.

The carbon composite particles can have a size of from 2 μm to 20 μm. The carbon composite particles can have a pore size of from 3 nm to 8 nm.

A solid acid catalyst includes an activated carbon particle of from 2 μm to 50 μm and having a plurality of pores having a pore size of from 1 nm to 10 nm, and a plurality of sulfonic acid groups joined to all sides of the surface of the activated carbon particles. The pyrolyzed carbon particles can have a size of from 2 μm to 20 μm.

BRIEF DESCRIPTION OF THE DRAWINGS

There are shown in the drawings embodiments that are presently preferred it being understood that the invention is not limited to the arrangements and instrumentalities shown, wherein:

FIG. 1A is TGA thermograms and FIG. 1B is the corresponding differential scanning calorimetry (DSC) of pyrolyzed waste tire carbon and the post-sulfonated tire-derived carbon (STC) and L-cysteine sulfonated tire carbon (STC-cys) catalysts in air.

FIGS. 3A, 3B, and 3C are SEM images of (FIG. 3A) pyrolyzed acid-treated waste tire carbon, (FIG. 3B) the STC catalyst, and (FIG. 3C) the STC-cys catalyst; and TEM images of (FIG. 3D) pyrolyzed acid-treated waste tire carbon, (FIG. 3E) the STC catalyst, and (FIG. 3F) the STC-cys catalyst.

FIG. 7A shows a time dependent study, FIG. 7B shows a variation in the amount of catalyst, FIG. 7C shows the effect of water, and FIG. 7D shows the results of a mercury poisoning experiment.

FIGS. 9A and 9B display SEM images of L-cysteine modified tire carbon. FIG. 9A is the SEM image indicating the porous microstructure of the STC-cys catalyst. FIG. 9B is the enlarged version of FIG. 9A.

DETAILED DESCRIPTION OF THE INVENTION

Figure 2:
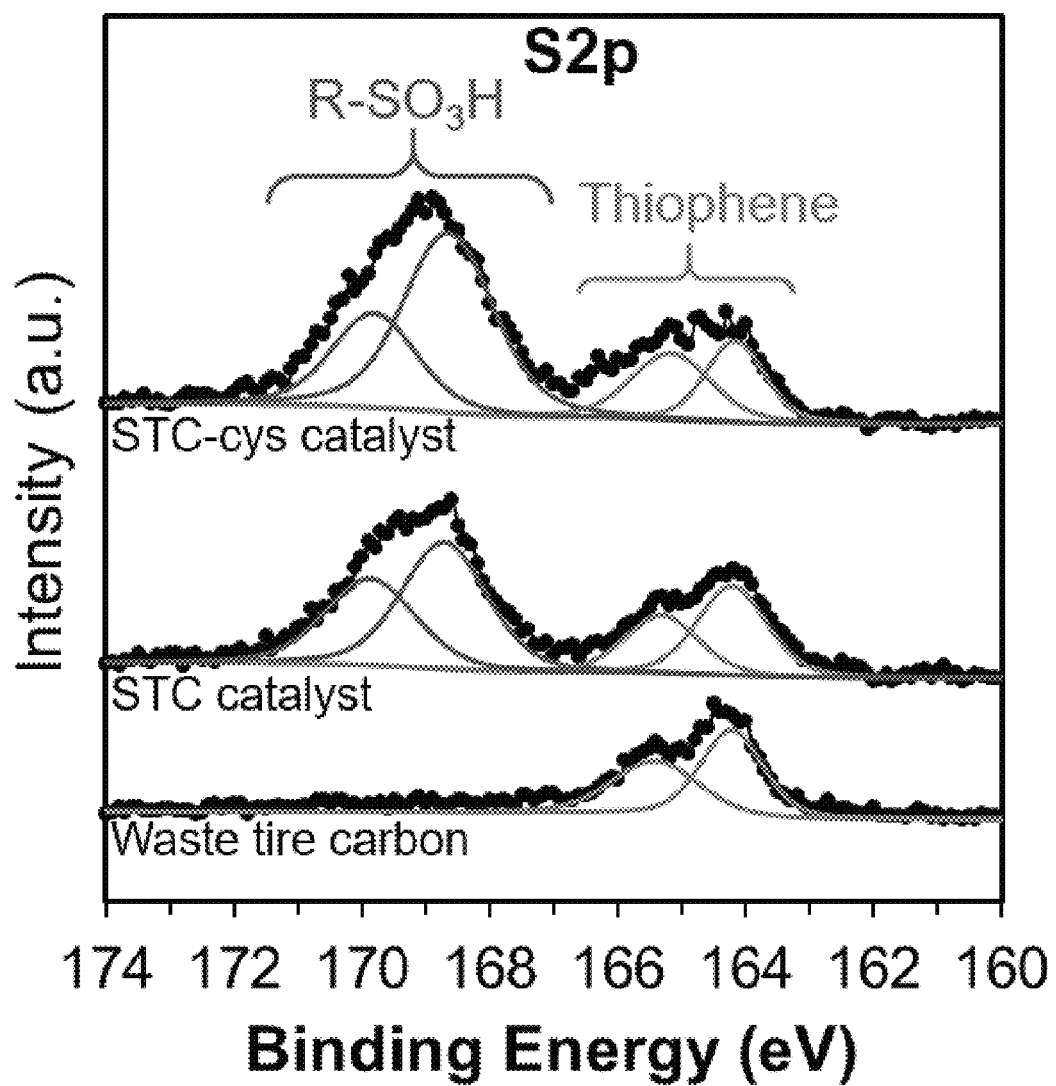
FIG. 2 is XPS spectra for the S2p peak for the pyrolyzed waste tire carbon, STC catalyst, and STC-cys catalyst.

A method of making solid acid catalysts includes the step of sulfonating waste tire pieces in a first sulfonation step. The sulfonated waste tire pieces are pyrolyzed to produce carbon composite pieces that can have a pore size less than 10 nm. The carbon composite pieces are then ground to produce carbon composite powders having a size less than 50 μm. The carbon composite powders can have a size of from 10 μm to 20 μm. The carbon particles can have a size of 2, 3, 4, 5, 6, 7, 8, 9, 10, 11, 12, 13, 14, 15, 16, 17, 18, 19, or 20 μm, or within a range of any high and low value selected from these values.

The carbon composite powders can have a pore size of from 3 nm to 8 nm. The carbon composite powders are sulfonated in a second sulfonation step to produce sulfonated solid acid catalysts. At least one of the sulfonation steps can be performed by soaking in a sulfuric acid bath. The sulfuric acid bath can be at least 5 M. The soaking can be for at least 10-20 minutes. The sulfonation bath can comprise any reactant composition capable of sulfonating rubber. It is also capable of sulfonating vulcanized particulate rubbers containing carbon black or carbon particles or carbon fiber or carbon nanomaterials. In one aspect the sulfonation bath can be an oleum bath. The oleum bath can comprise up to 65 wt. % $SO_3$ in concentrated sulfuric acid. Very high $SO_3$ content in oleum bath causes solidification of reactant mix and therefore, may not be useful for processing. The sulfonation bath can be a sulfuric acid ($H_2SO_4$) solution. The concentration of sulfuric acid in the oleum bath can be between 10 and 100 wt. %. The sulfonation bath can comprise other sulfonation agents such as chlorosulfonic acid in 1,2 dichloroethane solution, organic solvents (such as 1,2 dicholoroethane) containing $SO_3$ gas, or equimolar mixture of acetic anhydride concentrated sulfuric acid that yields acetyl sulfate. Acetyl sulfate assists in electrophilic sulfonation of aromatic ring in styrene containing rubbers but $SO_3$ can aid free radical sulfonation of aliphatic segments. Thus, the sulfonation bath can comprise a liquid, a gas, or a liquid and a gas. The sulfonation bath can comprise between 0.1-65 wt. % $SO_3$ in liquid medium that can be concentrated sulfuric acid or organic solvents. The sulfonation bath can comprise any minimum percentage and maximum percentage within this range, such as 5-20, 2-18, 2-30, or 0.1-2 wt. % $SO_3$. The sulfonation bath can have a temperature of between −20 to 200° C. The second sulfonation step can comprise contacting the carbon composite powders with L-cysteine with water and heat, followed by a reduction step and an oxidation step. The first sulfonation step can optionally also be performed by contact with L-cysteine.

The method can further comprise the step of washing the sulfonated waste tire pieces. The washed sulfonated waste tire pieces can be pressed and heated the washed sulfonated waste tire pieces into a sheet prior to the pyrolyzing step.

The pyrolyzing step can include heating the sulfonated waste tire pieces from 900° C. to 1500° C. The pyrolysis step can be conducted at a temperature that is greater than 400° C. The pyrolysis step can be conducted at a temperature that is greater than 1000° C. The pyrolysis step can be conducted at a temperature that is between 200-1000° C. The duration of the pyrolysis step can be from 1 minute to 12 hours or more. The conditions of the pyrolysis step such as temperature and duration can be selected depending on process conditions including the particular carbonaceous source material that is being pyrolyzed. The carbon content in pyrolyzed carbon materials can be higher than 80 wt. %.

The BET specific surface area in the pyrolyzed carbon particles can be modified by deploying a surface activation process. Surface activation processes are well known in art that produces activated carbon. Activated carbon can be synthesized from pyrolyzed carbon residues by activating it in steam or $CO_2$ at elevated temperature ranging from 200 to 1000° C. that results partially burnt out carbon residue with higher porosity. The added porosity by surface activation is usually microporosity with pore widths less than 50 nm. Activation of carbon can also be achieved by treating the particles with alkali followed by heat treatment in the presence of water vapors. The activated carbon particles can have a size of from 2 μm to 20 μm. The method activated carbon particles can have a pore size of from 3 nm to 8 nm.

The second sulfonation step follows the pyrolyzing step and the activation step. The second sulfonation step can be performed in a process similar to the first sulfonation step, or by a different process. Variations of the method are possible. In one embodiment, the first sulfonation step and second sulfonation step can be performed by contact with a sulfonation bath. In another embodiment, the first sulfonation step can be performed with a sulfonation bath and the second sulfonation step can be performed by a different process, such as contacting the carbon particles with L-cysteine. It is also possible to perform the invention without the first sulfonation step, and to instead perform sulfonation only after the pyrolyzing and activation steps. This may result in usable catalysts but with a lower yield. It may also be possible to use L-cysteine for sulfonation in the first sulfonation step.

The product of the invention is a carbon black containing catalyst product comprising a glassy carbon matrix phase having carbon black dispersed therein. The carbon black containing carbonaceous product is porous with a multi-modal pore size distribution with some pore width r, where 8 nm<r>120 nm and some pore width less than 8 nm but greater than 2 nm. The average pore size of the carbon black containing product can be between 2 and 120 nm. The average pore size can be between 3 and 8 nm. The average pore size can be 1, 2, 3, 4, 5, 6, 7, 8, 9 or 10 nm, or a range of any high or low of these values. The average pore size in some embodiments can be less than 2 nm. The carbon black containing product can have a Brunauer-Emmett-Teller (BET) specific surface area of less than 1000 $m^2/g$ depending on the continuity of carbon matrix. The specific surface area in composite can be less than 100 $m^2/g$.

A method of making biofuels includes the step of preparing a solid acid catalyst. The solid acid catalyst can be prepared by the steps of a) sulfonating waste tire pieces in a first sulfonation step; b) pyrolyzing the waste tire pieces to produce pyrolyzed sulfonated carbon having a pore size less than 10 nm; d) grinding the carbon composite powders to a particle size less than 50 μm; and, e) sulfonating the pyrolyzed sulfonated carbon in a second sulfonation step to produce sulfonated solid acid catalysts. A feedstock comprising free fatty acids is provided. The free fatty acids are esterified in the presence of the sulfonated solid acid catalysts.

The esterification can be performed in the presence of methanol. The free fatty acids can be either saturated or unsaturated. The free fatty acids can be at least one selected from the group consisting of formic acid, acetic acid, oleic acid, linoleic acid, linolinic acid, and palmitic acid, stearic acid, lauric acid, octadecadienoic acid, hexadecanoic acid, myristic acid, stearidonic acid, elaidic acid, gondoic acid, erucic acid, nervonic acid, mead acid, gadoleic acid, eicosenoic acid, erucic acid, pinolenic acid, stearidonic acid, arachidonic acid, eicosapentaenoic acid, and benzoic acid. The feedstock can include at least one selected from the group consisting of animal fats, waste cooking oil, and vegetable oil.

The second sulfonation step can optionally include contacting the carbon composite particles with L-cysteine to produce sulfur containing carbon particles, contacting the sulfur containing particles with a reducing agent to produce reduced sulfur containing particles, and oxidizing the reduced sulfur containing particles to produce sulfonated solid acid catalysts. The L-cysteine can be contacted with the carbon particles using a hydrothermal method followed by a reduction step to reduce any disulfide (—S—S—) bonds so formed in the surface to thiols (—S—H) and an oxidation of thiols to produce sulfonated solid acid catalysts.

A solid acid catalyst includes activated and sulfonated carbon particles of from 2 μm to 50 μm and having a plurality of pores having a pore size of from 1 nm to 10 nm, and a plurality of sulfonic acid groups joined to all sides of the surface of the activated carbon particles with at least 2-4 wt. % of sulfur content. As can be seen from Table 1, sulfur content increased from 3.62% to 5.81%. The total sulfur content after the second sulfonation can be 1, 2, 3, 4, 5, 6, 7, 8, 9, 10, 11, 12, 13, 14 or 15%, based on the total weight of the catalyst, or within a range of any high and low value selected from these values. The total sulfur content can increase 2, 3, 4, 5, 6, 7, 8, 9 or 10%, or a range of any high and low value selected from these values, after the second sulfonation step. The activated carbon particles can have a size of from 2 μm to 20 μm.

Crum rubber pieces (<0.5 inch in size) from a recycled tire were used to derive carbon by soaking in concentrated sulfuric acid bath that was kept at 110° C. for several days and subsequent washing. The washed sulfonated tire rubber cake was then pressed between Teflon sheets under a hot plate inside a compression mold at 110° C. to remove moisture and to obtain a thick (2 mm) molded sheet, followed by pyrolysis in a tubular furnace under a flowing nitrogen gas atmosphere at 1100° C. The temperature of the furnace was ramped up from room temperature to 1100° C. at 10° C./min; upon reaching 1100° C., the temperature was maintained for 15 min followed by cooling to room temperature, to extract the carbon (Yield: up to 50%). The pyrolyzed acid-treated carbon was further soaked in concentrated sulfuric acid to yield thermally stable catalysts. The post-sulfonated pyrolyzed tire-derived carbon is designated as STC and STC-cys carbon catalysts. The elemental analysis of both pyrolyzed acid-treated carbon and STC catalyst are reported in Table 1. As can be seen in Table 1, increased concentrations of —$SO_3H$ is observed in STC carbon catalysts.

TABLE 1

Elemental Analysis of pyrolyzed acid-treated waste tire rubber before, after sulfonation in $H_2SO_4$ (STC catalyst), and after sulfonation with L-cysteine (STC-cys catalyst).

|  | % C | % H | % N | % S | % O* |
| --- | --- | --- | --- | --- | --- |
| Pyrolyzed acid-treated tire rubber | 87.14 ± 0.16 | 0.23 ± 0.01 | 0.30 ± 0.04 | 3.62 ± 0.10 | 8.51 |
| STC carbon catalyst | 77.45 ± 2.20 | 1.22 ± 0.11 | 0.61 ± 0.01 | 5.81 ± 0.12 | 13.53 |
| Sulfonated tire carbon from L-cysteine (STC-cys) catalyst | 80.71 ± 1.61 | 0.77 ± 0.16 | 0.41 ± 0.01 | 4.78 ± 0.31 | 13.33 |

*The % O was determined by the difference of the other organics in the samples analyzed.

Thermogravimetric analysis (TGA) and differential scanning calorimetry (DSC) of the STC catalyst was conducted to determine its compositional characteristics. The TGA and DSC on the pyrolyzed waste tire-derived carbon and the STC and STC-cys catalysts are shown in FIG. 1. The first weight loss in STC catalyst could be due to the loss of water followed by the elimination of $H_2SO_4$ starts around 150° C. followed by desulfonation process occurs between 400-600° C. The surface chemistry before and after sulfonation process is determined with X-ray Photoelectron Spectroscopy (XPS). The XPS spectra for the S2p peak for (a) pyrolyzed waste tire carbon after digestion in sulfuric acid bath, (b) the STC catalyst and (c) the STC-cys catalyst are shown in FIG. 2. The doubles at about 164 eV are related to the thiophenic group and the peak at 169 eV is due to the presence of the sulfonic acid group. It is shown that the sulfonic acid group is distinctly observed in the STC and STC-cys carbon catalysts. In addition, the surface chemistry before and exhaustive leaching process is determined with XPS. Scanning electron microscopy (SEM) and Transmission electron microscopy (TEM) images of both pyrolyzed acid-treated waste tire carbon and the STC and STC-cys catalysts are shown in FIG. 3.

Figure 4:
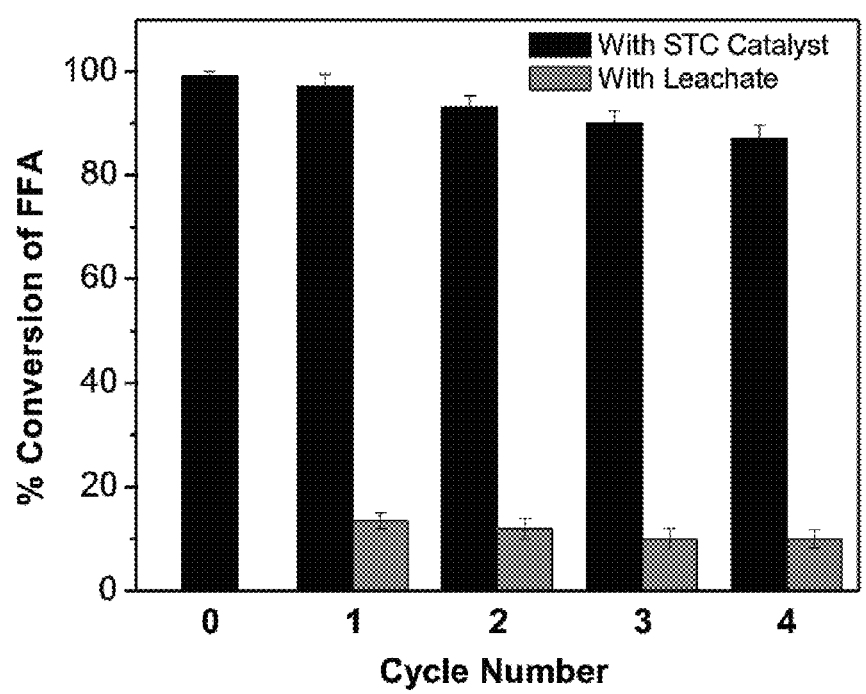
FIG. 4 is a catalytic activity of the pristine STC catalyst and after each exhaustive leaching cycle.
Figure 5:
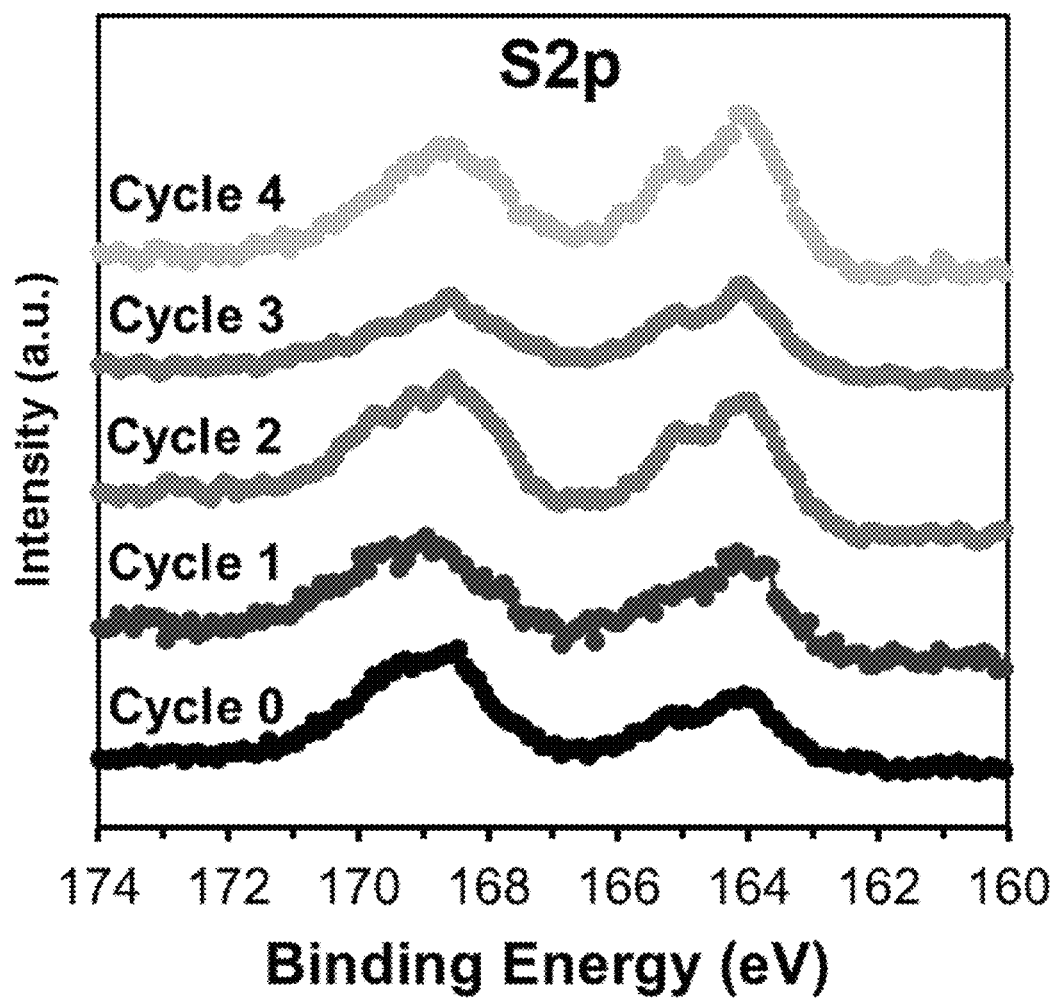
FIG. 5 is XPS spectra of the S2p peak of the STC catalyst and after each methanol extraction cycle.

The catalytic activity testing was conducted using 10:1 methanol to oleic acid concentration with 10 wt. % of the STC carbon catalyst. The leaching of the catalyst was performed with 80 mL of methanol and 2.0 grams of the STC carbon catalyst. The catalytic activities of the pristine STC catalyst and after 4 cycles of leaching are shown in FIG. 4. The bar charts in FIG. 4 displays the catalytic activity in terms of % conversion of the FFA to the corresponding ester. The XPS of the STC catalyst after 4 cycles of leaching is shown in FIG. 5. The XPS results show little change in the oxidation, supporting the robustness of this catalyst. The doubles at about 164 eV and the peak at 169 eV are preserved after each cycles. It is shown that the —$SO_3H$ sulfate group is observed in STC carbon catalyst after $4^{th}$ cycle. This provides direct evidence for preservation of the catalyst and that the catalyst can be recycled. Similar results were obtained for the STC-cys catalyst.

Figure 6:
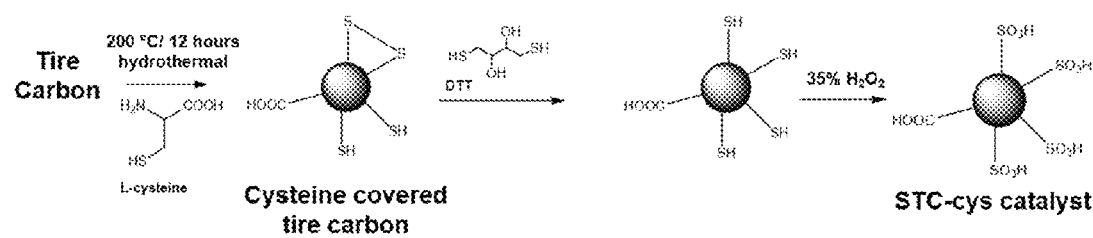
FIG. 6 is a scheme of the synthesis of L-cysteine modified sulfonated tire carbon (STC-cys).

The synthesis of L-cysteine-modified tire carbon (sulfonated and pyrolyzed) was completed through a hydrothermal treatment followed by reduction and oxidation steps as shown in FIG. 6. In a typical method, 1.0 g of tire carbon (TC) was ground with 1.0 g of L-cysteine for 5 minutes and then dispersed in 60 mL of deionized water. The mass was transferred to a Teflon-lined autoclave (capacity, 100 mL) and heated to 200° C. for 12 hours. The resulting solid mass was filtered and washed thoroughly with deionized water and dried in vacuum oven (at 60° C.) for 4 hours. The second step involves reduction using common reducing agent DTT (Dithiothreitol). During the reduction step, the dried mass was dispersed in 25 mL of deionized water and 2.0 g of DDT was added, and the mixture was stirred vigorously. During the process, the pH of the solution was maintained basic (around 10) using the 1 M NaOH solution. It was stirred for 2 hours at room temperature. After the reduction step, the solid mass was filtered and then transferred to a new flask. For the oxidation step, the solid mass obtained from the filtration was treated in 30 mL of 30% hydrogen peroxide under magnetic stirring for 2 hours at room temperature. Finally, the L-cysteine-modified tire carbon has been recovered from filtration.

Figure 7A:
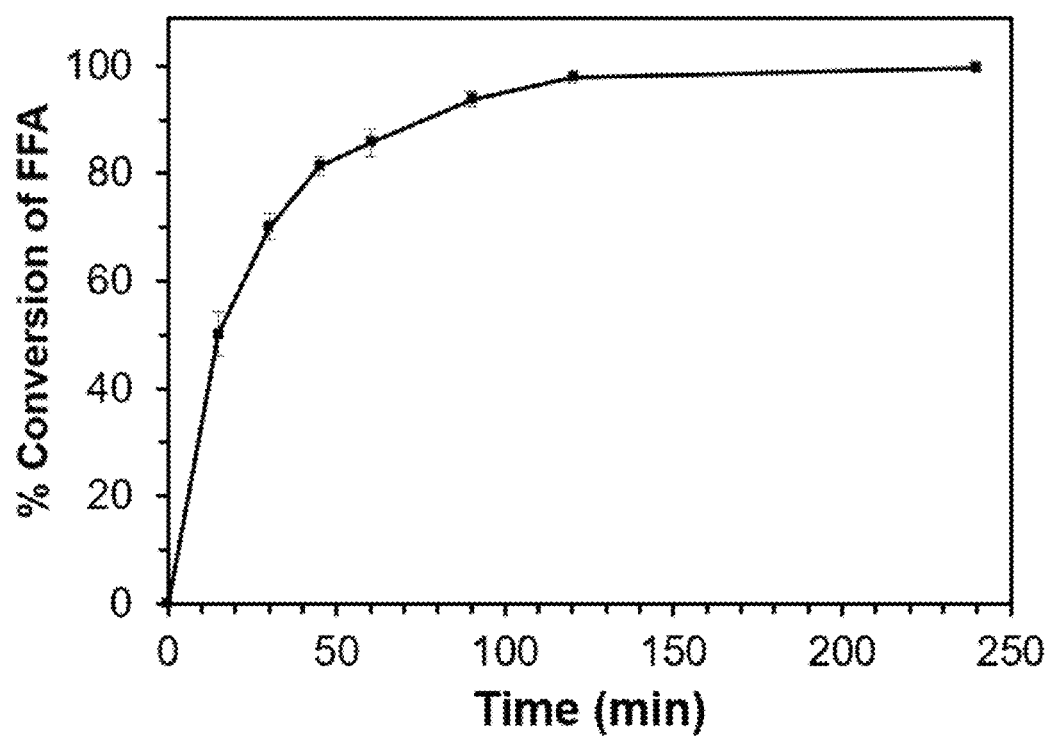
FIGS. 7A, 7B, 7C and 7D show the activity data for the STC catalyst.
Figure 7B:
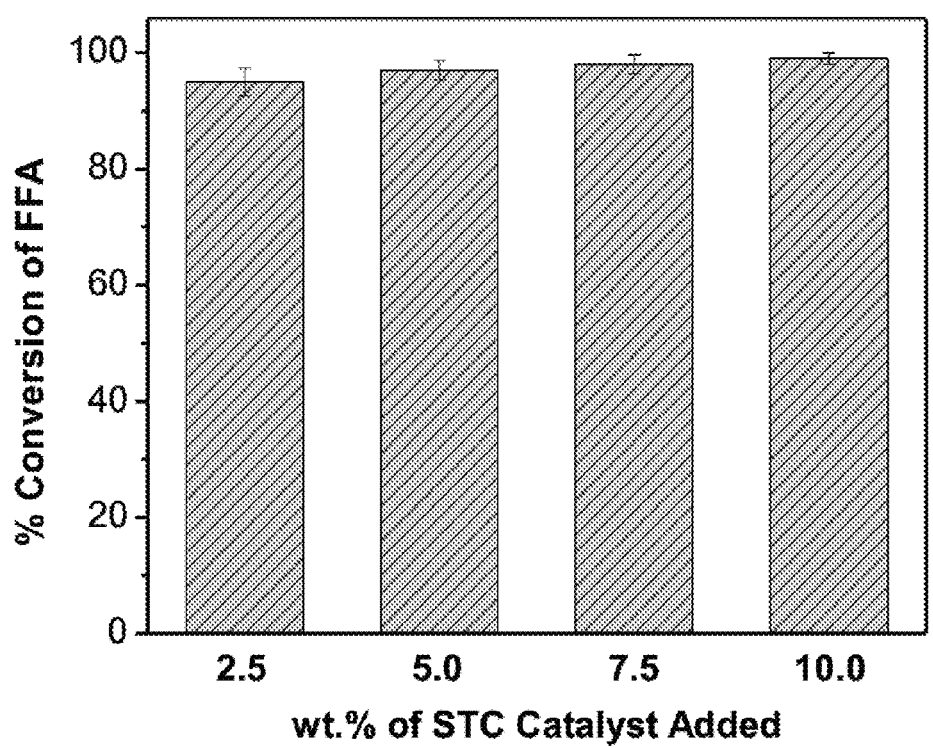
Figure 7C:
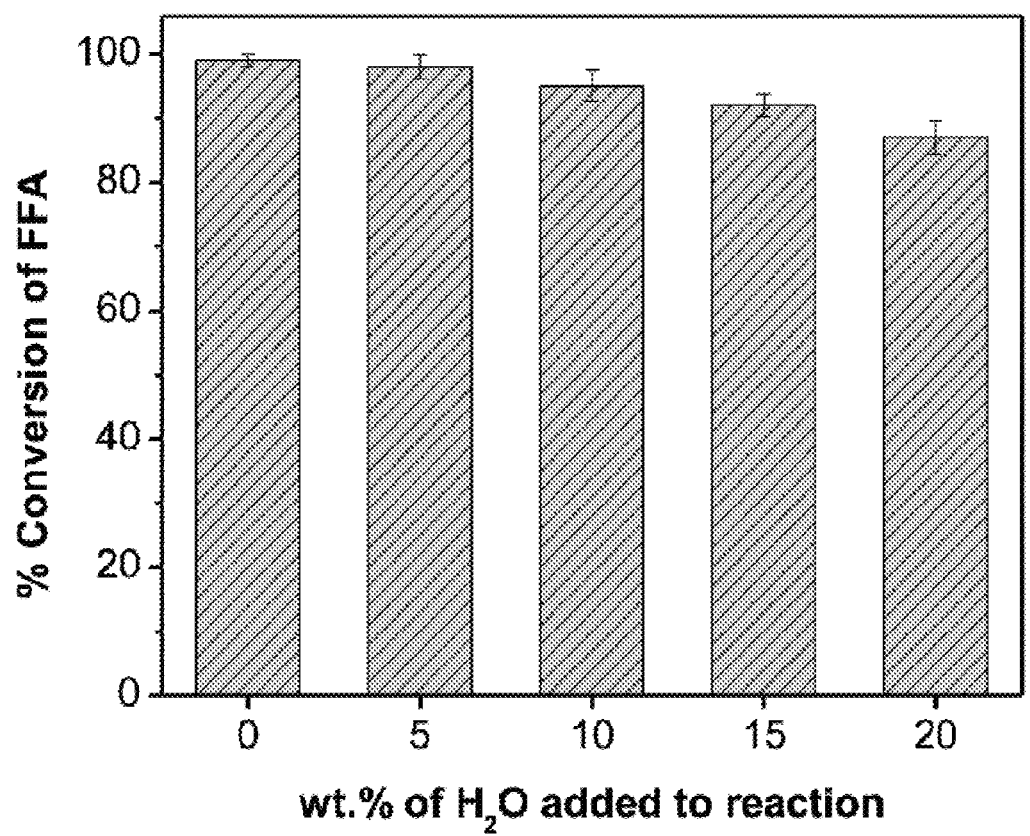
Figure 7D:
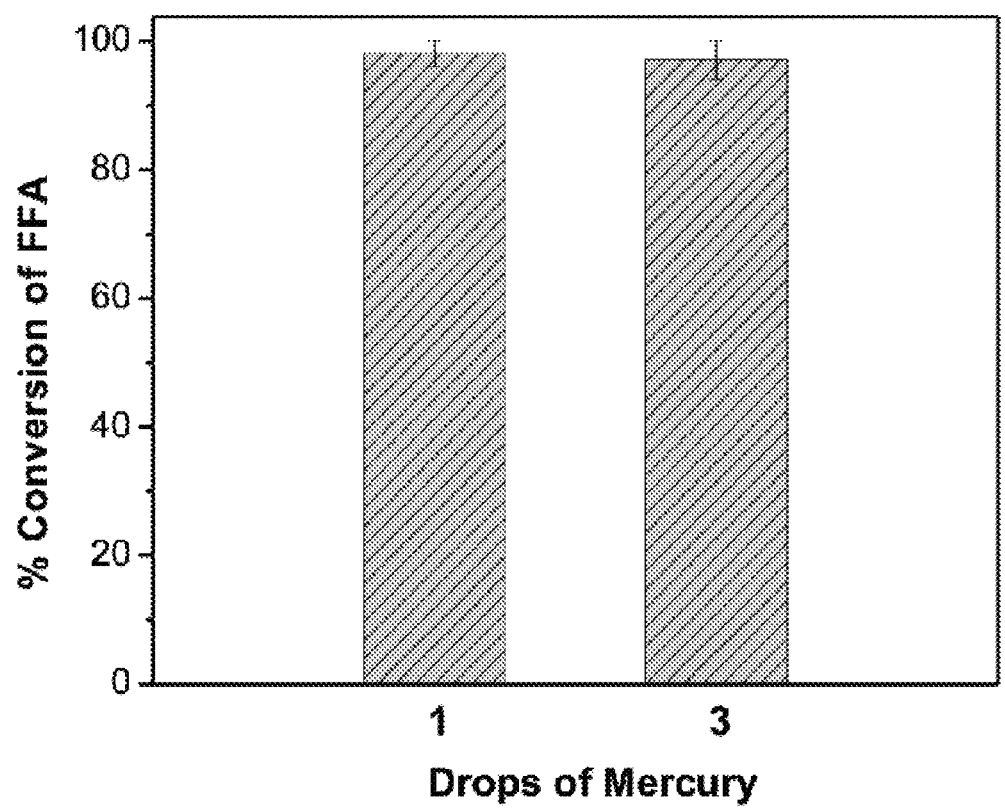

FIGS. 7A, 7B, 7C and 7D show the activity data on the conversion of FFA into biofuel for the STC catalyst. FIG. 7A shows the time dependent study, FIG. 7B shows the variation amount of catalyst, FIG. 7C shows the effect of water and FIG. 7D shows the mercury poisoning experiment. The L-cysteine-modified tire carbon catalyst displays similar catalytic activity.

Figure 8:
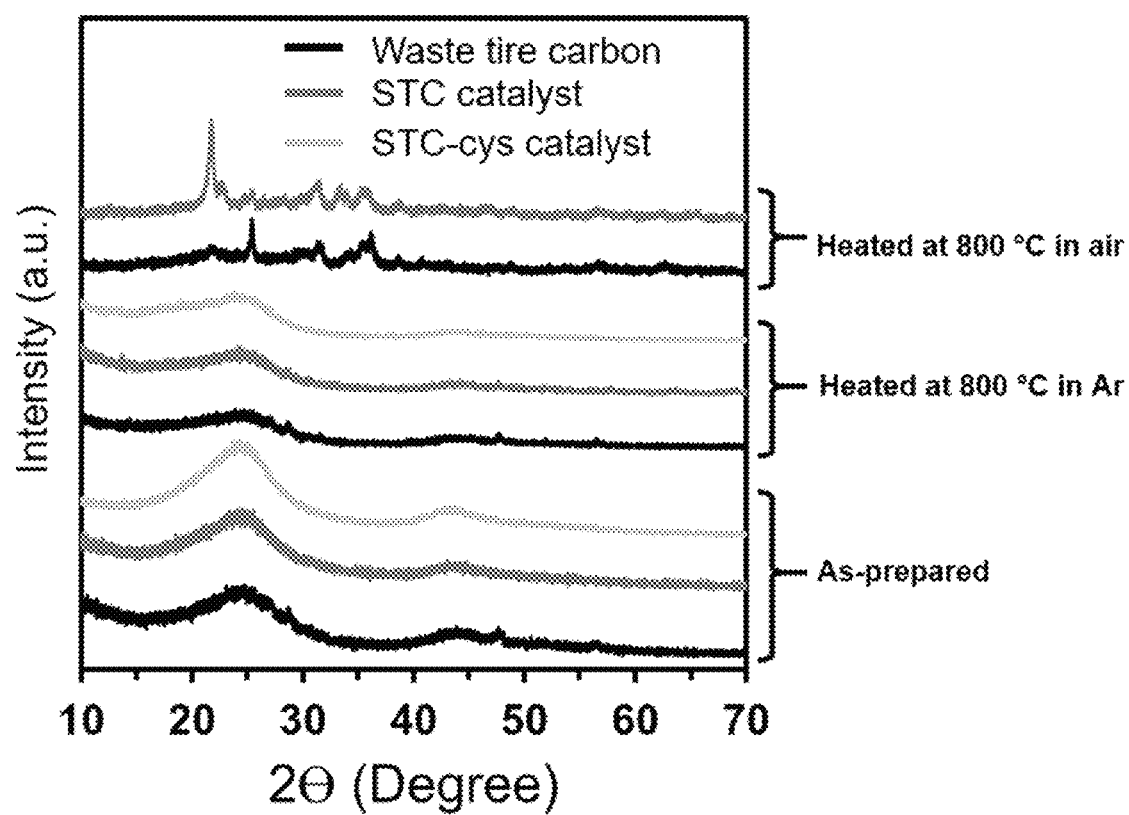
FIG. 8 displays the XRD patterns of tire carbon, the STC catalyst, and the STC-cys catalyst under ambient conditions and after heating to 800° C. in air and Argon.

FIG. 8 is a XRD of L-cysteine-modified tire carbon with broader peaks indicating the non-crystalline nature of the carbon.

FIG. 9 is a SEM of L-cysteine modified tire carbon indicating the porous microstructure of carbon.

Figure 10:
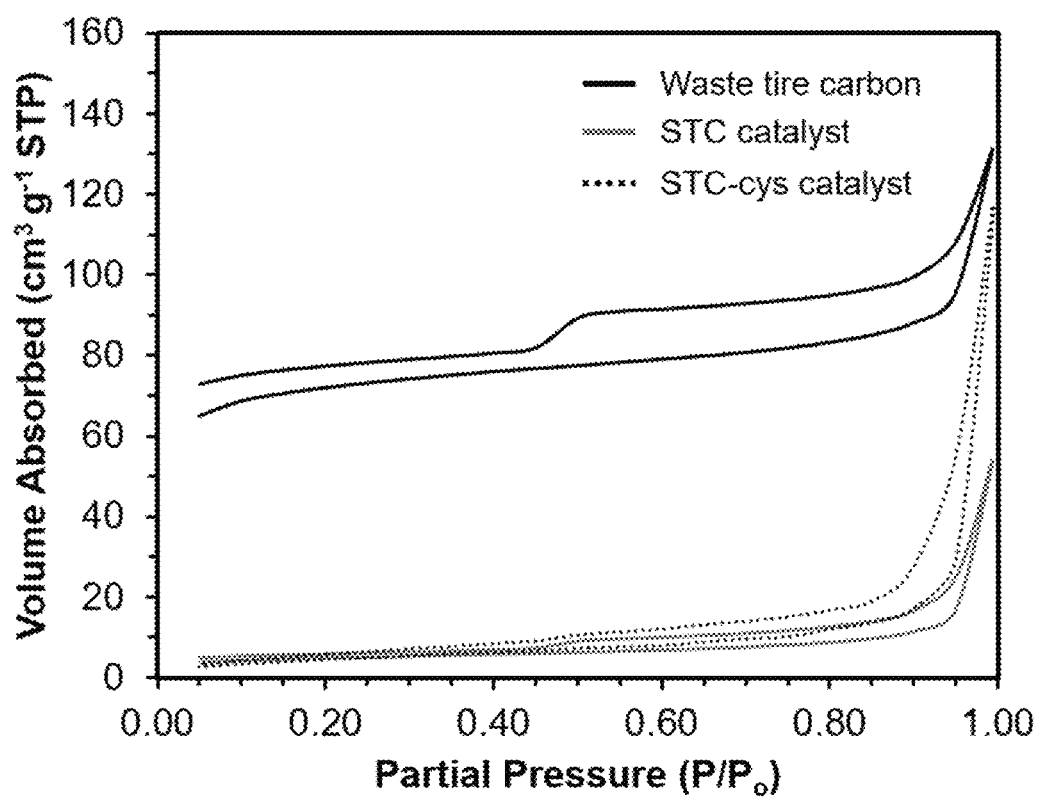
FIG. 10 is a BET of tire carbon, the STC catalyst, and the STC-cys catalyst.

FIG. 10 is a nitrogen adsorption desorption isotherm of the tire carbon, the STC catalyst, and the STC-cys catalyst L-cysteine, confirming the porous nature of carbon with determined pore volume and pore size distribution of 0.07878 cc $g^{-1}$ and 3.824 nm for the STC catalyst and 0.17700 cc $g^{-1}$ and 3.820 nm for the STC catalyst.

Figure 11A:
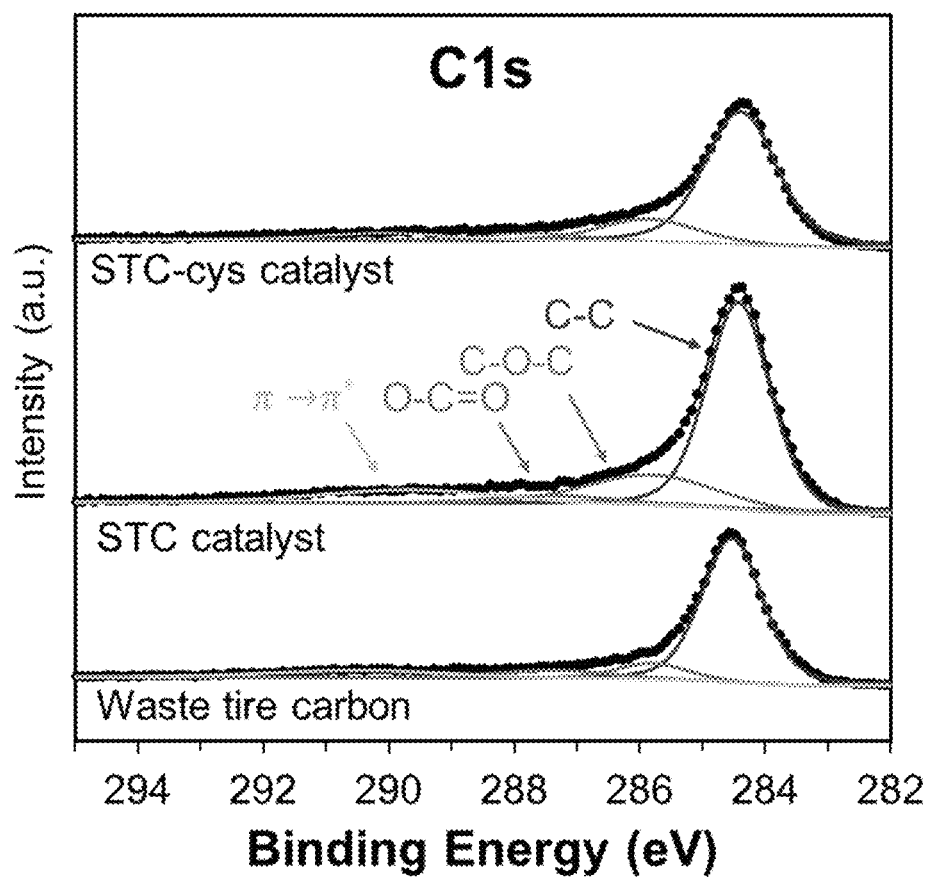
FIGS. 11A and 11B are XPS for C1s and O1s, respectively, of tire carbon, the STC catalyst, and the STC-cys catalyst.
Figure 11B:
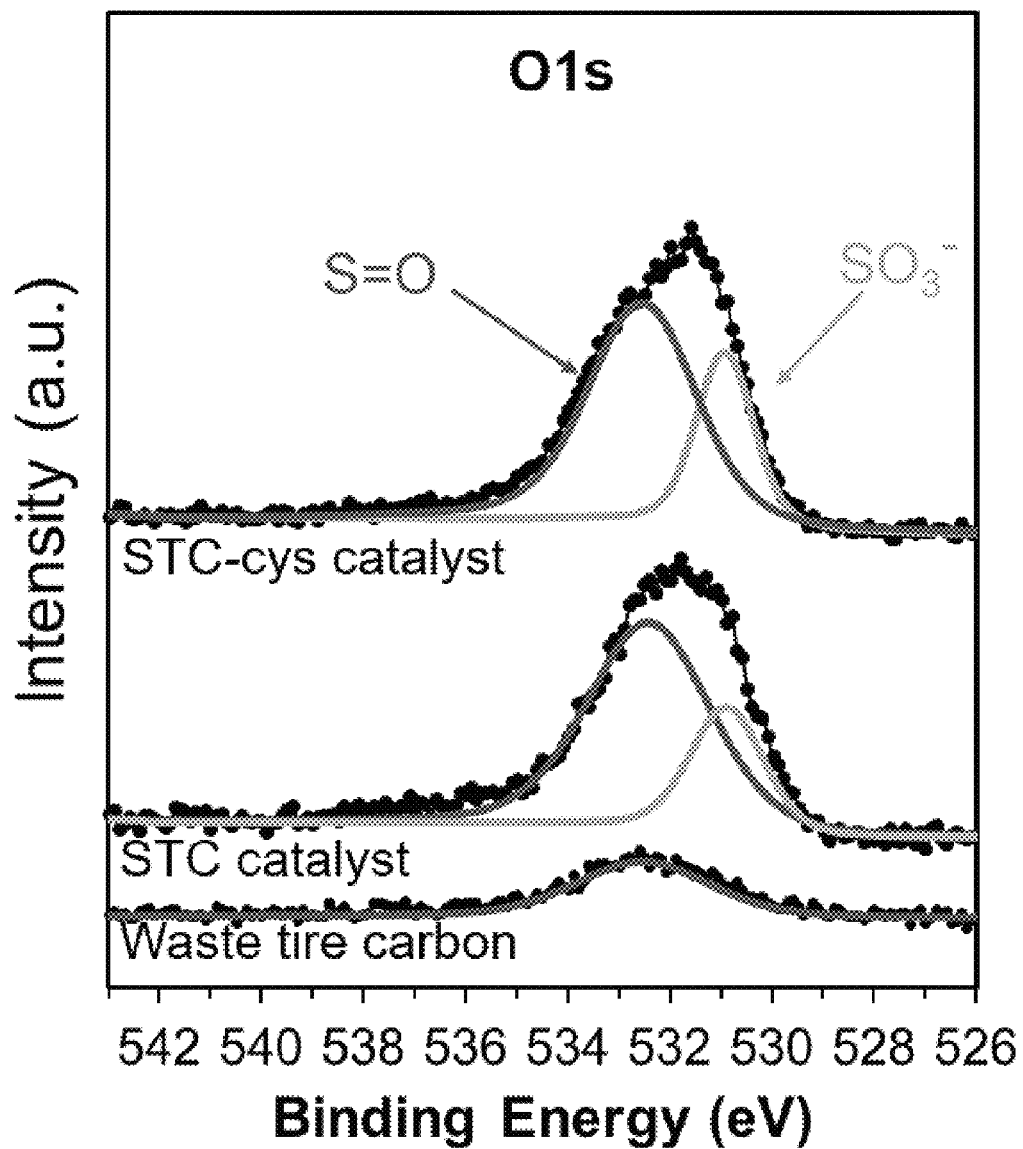

FIGS. 11A and 11B are XPS of tire carbon, the STC catalyst, and the STC-cys catalyst for the C1s region, which indicate the presence of C—C bond, C—O—C bond, C—C═O and other pi-pi bonds, and XPS for the O1s region, which indicate the presence of $SO_3^-$ and S═O, respectively.

The method can include a step of reducing the carbonaceous source material such as waste tires to a powder prior to the first sulfonation and pyrolyzing steps. The powder can be formed by any suitable method such as grinding, milling, cutting, and cryogenic pulverization. The powder so formed can have an average maximum dimension of less than 100 nm to 10 cm. Also, crumb rubber with a size of less than 10 cm wide can also be used without grinding. Metal particles such as Ni, stainless steel, Iron, and oxides such as ZnO, $SiO_2$ and others present along with carbonaceous source material may also dissolve in the oleum bath and yield carbon powder with no metals and/or oxides or up to ppm levels of metals. The presence of Ca comes from kaolin or talc filler in rubber compounds and can form insoluble sulfates by reaction with sulfonating agents such as, for example, sulfuric acid. To avoid such impurities, if required, the tire rubbers can be washed with aqueous hydrochloric acid, nitric acid, or an acidic salt (for example ammonium chloride) solution prior to sulfonation.

In addition to waste tires, the carbonaceous source material can be any suitable carbon black containing source material. One such source material comprises carbon black loaded plastics, scrap electronic casing containing carbon black loaded plastics that serve as electromagnetic shielding material, polymeric carbon nanocomposites containing carbon particles, and carbon fiber reinforced composites. The carbonaceous source material can be a waste material, such as scrap vulcanized rubber tires or recycled vulcanized rubbers from other sources. Also the cysteine modified tire derived carbon solid acid catalysts may be used in cracking such as alkylation where the combination of benzene and ethylene to form ethylbenzene and also the formation of alkylamines using amination of alcohols.

This invention can be embodied in other forms without departing from the spirit or essential attributes thereof, and accordingly reference should be had to the following claims to determine the scope of the invention.

We claim:

1. A method of making solid acid catalysts, comprising the steps of:
   sulfonating the waste tire pieces in a first sulfonation step;
   pyrolyzing waste tire pieces to produce carbon composite pieces having a pore size less than 10 nm;
   grinding the carbon composite pieces to produce carbon composite particles having a particle size less than 50 µm;
   sulfonating the carbon composite particles in a second sulfonation step to produce sulfonated solid acid catalysts.

2. The method of claim 1, wherein at least one of the sulfonation steps is performed by soaking in a sulfuric acid bath.

3. The method of claim 2, wherein the sulfuric acid bath is at least 5 M.

4. The method of claim 2, wherein the sulfuric acid bath has a temperature of between −20° C. to 200° C.

5. The method of claim 2, wherein the soaking is for at least 10-20 minutes.

6. The method of claim 1, further comprising the step of washing the sulfonated waste tire pieces.

7. The method of claim 6, further comprising the step of pressing and heating the washed sulfonated waste tire pieces into a sheet prior to the pyrolyzing step.

8. The method of claim 1 wherein the pyrolyzing step comprises heating the sulfonated waste tire pieces to from 900° C. to 1500° C.

9. The method of claim 1, wherein the second sulfonation step comprises contacting the carbon composite particles with L-cysteine with water and heat, followed by a reduction step and an oxidation step.

10. The method of claim 1, wherein the carbon composite particles have a size of from 2 µm to 20 µm.

11. The method of claim 1, wherein the carbon composite particles have a pore size of from 3 nm to 8 nm.

12. A method of making biofuels, comprising the steps of:
    preparing a solid acid catalyst, the solid acid catalyst being prepared by the steps of:
    a) sulfonating waste tire pieces in a first sulfonation step
    b) pyrolyzing the waste tire pieces to produce carbon composite pieces having a pore size less than 10 nm;
    c) grinding the carbon composite pieces to carbon composite particles having size less than 50 µm; and,
    d) sulfonating the carbon composite particles in a second sulfonation step to produce sulfonated solid acid catalysts;
    providing feedstock comprising free fatty acids;
    esterifying the free fatty acids in the presence of the sulfonated solid acid catalysts.

13. The method of claim 12, wherein the pyrolyzing step comprises heating the sulfonated waste tire pieces to from 900° C. to 1500° C.

14. The method of claim 12, wherein the esterification is performed in the presence of methanol.

15. The method of claim 12, wherein the free fatty acids comprise at least one selected from the group consisting of saturated and unsaturated free fatty acids.

16. The method of claim 12, wherein the free fatty acids comprise at least one selected from the group consisting of formic acid, acetic acid, oleic acid, linoleic acid, linolinic acid, palmitic acid, stearic acid, octadecadienoic acid, hexadecanoic acid, myristic acid, stearidonic acid, elaidic acid, gondoic acid, erucic acid, nervonic acid, mead acid, gadoleic acid, eicosenoic acid, erucic acid, pinolenic acid, stearidonic acid, arachidonic acid, eicosapentaenoic acid, and benzoic acid.

17. The method of claim 12, wherein the feedstock comprises at least one selected from the group consisting of animal fats, waste cooking oil, and vegetable oil.

18. The method of claim 12, wherein the second sulfonation step comprises contacting the carbon composite particles with L-cysteine using a hydrothermal method followed by a reduction step and an oxidation step to produce sulfonated solid acid catalysts.

19. The method of claim 12, wherein the carbon composite particles have a size of from 2 µm to 20 µm.

20. The method of claim 12, wherein the carbon composite particles have a pore size of from 3 nm to 8 nm.

21. A solid acid catalyst, comprising:
    an activated carbon particle of from 2 µm to 50 µm and having a plurality of pores having a pore size of from 1 nm to 10 nm;
    a plurality of sulfonic acid groups joined to all sides of the surface of the activated carbon particles.

22. The solid acid catalyst of claim 21, wherein the activated carbon particles have a size of from 2 µm to 20 µm.

* * * * *